United States Patent
Willocq et al.

(10) Patent No.: US 10,604,470 B2
(45) Date of Patent: Mar. 31, 2020

(54) METHOD FOR PURIFYING AN AQUEOUS LACTIC ACID SOLUTION

(71) Applicant: Futerro S.A., Escanaffles (BE)

(72) Inventors: Jonathan Willocq, Escanaffles (BE); Philippe Coszach, Escanaffles (BE); Jean-Christophe Bogaert, Escanaffles (BE)

(73) Assignee: Futerro S.A., Escanaffles (BE)

( * ) Notice: Subject to any disclaimer, the term of this patent is extended or adjusted under 35 U.S.C. 154(b) by 0 days.

(21) Appl. No.: 16/096,152

(22) PCT Filed: May 11, 2017

(86) PCT No.: PCT/EP2017/061386
§ 371 (c)(1),
(2) Date: Oct. 24, 2018

(87) PCT Pub. No.: WO2017/194700
PCT Pub. Date: Nov. 16, 2017

(65) Prior Publication Data
US 2019/0135728 A1 May 9, 2019

(30) Foreign Application Priority Data

May 11, 2016 (BE) .................................. 2016/5333

(51) Int. Cl.
| | | |
|---|---|---|
| *C07C 51/44* | (2006.01) | |
| *C07C 51/48* | (2006.01) | |
| *B01D 3/00* | (2006.01) | |
| *B01D 3/14* | (2006.01) | |
| *B01D 3/28* | (2006.01) | |
| *B01D 3/32* | (2006.01) | |
| *C07C 59/08* | (2006.01) | |

(52) U.S. Cl.
CPC ............ *C07C 51/44* (2013.01); *B01D 3/005* (2013.01); *B01D 3/148* (2013.01); *B01D 3/28* (2013.01); *B01D 3/322* (2013.01); *C07C 51/48* (2013.01); *B01D 3/146* (2013.01); *C07C 59/08* (2013.01)

(58) Field of Classification Search
CPC ..................................................... C07C 51/44
USPC ........................................................ 562/580
See application file for complete search history.

(56) References Cited

U.S. PATENT DOCUMENTS

| 1,594,843 A | 8/1926 | Lawrie |
| 8,592,609 B2 | 11/2013 | Coszach et al. |
| 8,791,228 B2 | 7/2014 | Sirol |

FOREIGN PATENT DOCUMENTS

| WO | 1998/055442 A1 | 12/1998 | |
| WO | WO-9855442 A1 * | 12/1998 | ............. C07C 51/47 |
| WO | 2001/038283 A1 | 5/2001 | |

OTHER PUBLICATIONS

Gilnos et al: "Design of Sidestream Distillation Columns", Industrial and Engineering Chemistry Process Design and Development, vol. 24, No. 3, pp. 822-828 (Year: 1985).*
Gilnos, Konstantinos N., et al., "Design of Sidestream Distillation Columns," Industrial and Engineering Chemistry Process Design and Development, 1985, vol. 24, pp. 822-828.
International Search Report, International Application No. PCT/EP2017/061386, dated Aug. 18, 2017, 3 pages.

* cited by examiner

*Primary Examiner* — Deborah D Carr
(74) *Attorney, Agent, or Firm* — Fitch, Even, Tabin & Flannery LLP

(57) ABSTRACT

The present invention concerns a method for purifying an aqueous lactic acid solution, obtained from a fermentation medium or from any other source previously cleared of solid substances and/or of biomass that may be present and ionic substances, characterised in that it comprises the two following steps: a. Concentration of the lactic acid solution until a concentration of between 85 and 95% is reached, preferably of between 90 and 95%, i.e. between 15 and 5% free water or preferably between 10 and 5% free water; b. Distillation in a multi-stage column comprising three areas and allowing the separation, in a single step, of the lactic acid, volatile compounds and the heaviest impurities.

20 Claims, 1 Drawing Sheet

METHOD FOR PURIFYING AN AQUEOUS LACTIC ACID SOLUTION

SUBJECT OF THE INVENTION

The present invention relates to a process for purifying an aqueous lactic acid solution, obtained from a fermentation medium or from any other source previously stripped of the solid substances and/or of the biomass optionally present and also of the ionic substances.

PRIOR ART

Several industrial processes for polymerizing lactic acid have been developed in recent years with more or less success. One of the preferred routes for producing PLA being ring-opening polymerization. However, irrespective of the route envisaged (ring opening or polycondensation), it requires an initial lactic acid of very high purity and therefore that is stripped of the impurities resulting from the fermentation of sugars or from degradation phenomena that may occur during its production.

Patent EP 0 986 532 describes a process for purifying lactic acid obtained by fermentation comprising a pretreatment on ion columns, a double step of concentrating the lactic acid solution with the elimination of all of the free water and a distillation of the concentrated acid. However, although this process generates a quality lactic acid for most applications of the conventional market, it does not allow an optimal separation of the impurities, such as the organic monoacids or diacids, the alcohols, the aldehydes, etc. during the purification steps. Indeed, some of these impurities have volatilities such that they are found in the purified lactic acid. Yet these impurities give rise, during the lactide synthesis steps (cyclization of lactic acid), to an increase in the color during the polycondensation step or a "blocking" of the backbiting reaction. Furthermore, they are also likely to be able to deactivate the polymerization or cyclization catalysts commonly used.

U.S. Pat. No. 1,594,843 describes a technique for purifying lactic acid by flash distillation of an aqueous lactic acid solution. No reference is made as regards the volatile impurities capable of disrupting the polymerization, nevertheless it appears obvious to a person skilled in the art that a flash distillation does not make it possible to obtain a sufficient selectivity to separate the various volatile constituents of a solution.

Patent EP 1 232 137 itself describes a technique for purifying an aqueous lactic acid solution with the aid of at least two distillation steps, the solution being vaporized during the first distillation step and transported to a distillation column. The fact of resorting to two successive distillation steps implies both significant investment costs and also very high operating, mainly energy, costs. Furthermore, the longer residence times due to the presence of two successive columns results in more numerous degradations that have an impact on the purity and the color of the final lactic acid.

There is therefore a need for an economically efficient method for purifying lactic acid that enables the elimination both of the non-volatile impurities and of the volatile impurities of acid or alcohol type so as to obtain a purified lactic acid of a grade that enables the polymerization thereof under optimal conditions for the production of polylactic acid.

CHARACTERISTIC FEATURES OF THE INVENTION

The present invention relates to a process for purifying an aqueous lactic acid solution, obtained from a fermentation medium or from any other source previously stripped of the solid substances and/or of the biomass optionally present and also of the ionic substances, characterized in that it comprises the following two steps:
  a. concentrating the lactic acid solution until a concentration of between 85% and 95%, preferentially between 90% and 95%, i.e. 15% to 5% of free water or preferentially 10% to 5% of free water, is achieved;
  b. performing a distillation in a multistage column comprising three zones and enabling the separation, in a single step, of the lactic acid, the volatile compounds and the heavier impurities.

DETAILED DESCRIPTION OF THE INVENTION

Figure 1:
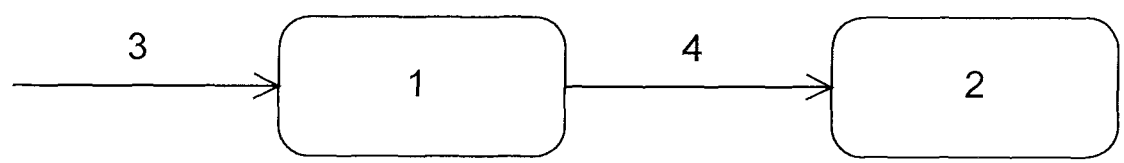
FIG. 1 schematically shows the process for purifying lactic acid according to one embodiment of the present invention.

The present invention describes a process for purifying lactic acid originating from an aqueous solution of this acid such as obtained from a fermentation medium or from any other source previously stripped of the solid substances and/or of the biomass optionally present and also of the ionic substances by any technique known to a person skilled in the art such as for example ion-exchange resins, the use of quaternized fatty amines, chromatography, etc. FIG. 1 illustrates the process for purifying lactic acid (LA) as is referred to in the present invention. This process of the invention essentially comprises the following steps:
  1. Concentration of the Lactic Acid Solution This step of the invention consists of the rapid, low-temperature concentrating of the lactic acid solution until a concentration of between 85% and 95%, preferentially between 90% and 95%, is achieved. A preferred approach of the present invention envisages carrying out this evaporation under reduced pressure, maintained between 40 and 500 mbar absolute (mbara) and preferably between 50 and 250 mbar, in order to ensure as low as possible a boiling point of the solution. This step of the invention is carried out by any technique known to a person skilled in the art such as, for example, thin-film and more particularly falling film evaporation. A preferred mode of this step of the invention is to use a technique that enables a minimal residence time in order to reduce oligomerization and thus improve the overall yield.

According to one preferred embodiment of the process of the invention, this step is directly followed by the distillation step, that is to say there is no storage period of the concentrated lactic acid solution between the two steps of the process. However, according to another embodiment of the process of the invention, it is possible, in order to facilitate the transfer between the step of concentrating the lactic acid solution and the distillation step, to provide a limited storage period of the concentrated lactic acid solution, that is to say a period of between 0 and 24 h, preferentially between 0 and 120 min, more preferentially between 0 and 15 min, before transferring it to the distillation step. In this particular embodiment of the process of the invention and as a function of the storage temperature, the impact of this storage period will be more or less pronounced (e.g.: storage, even prolonged storage (48 h or more) at a temperature below 20° C. will have a lower impact than a storage of 2 h at 140° C.).

2. Purification of Lactic Acid by Distillation

Figure 2:
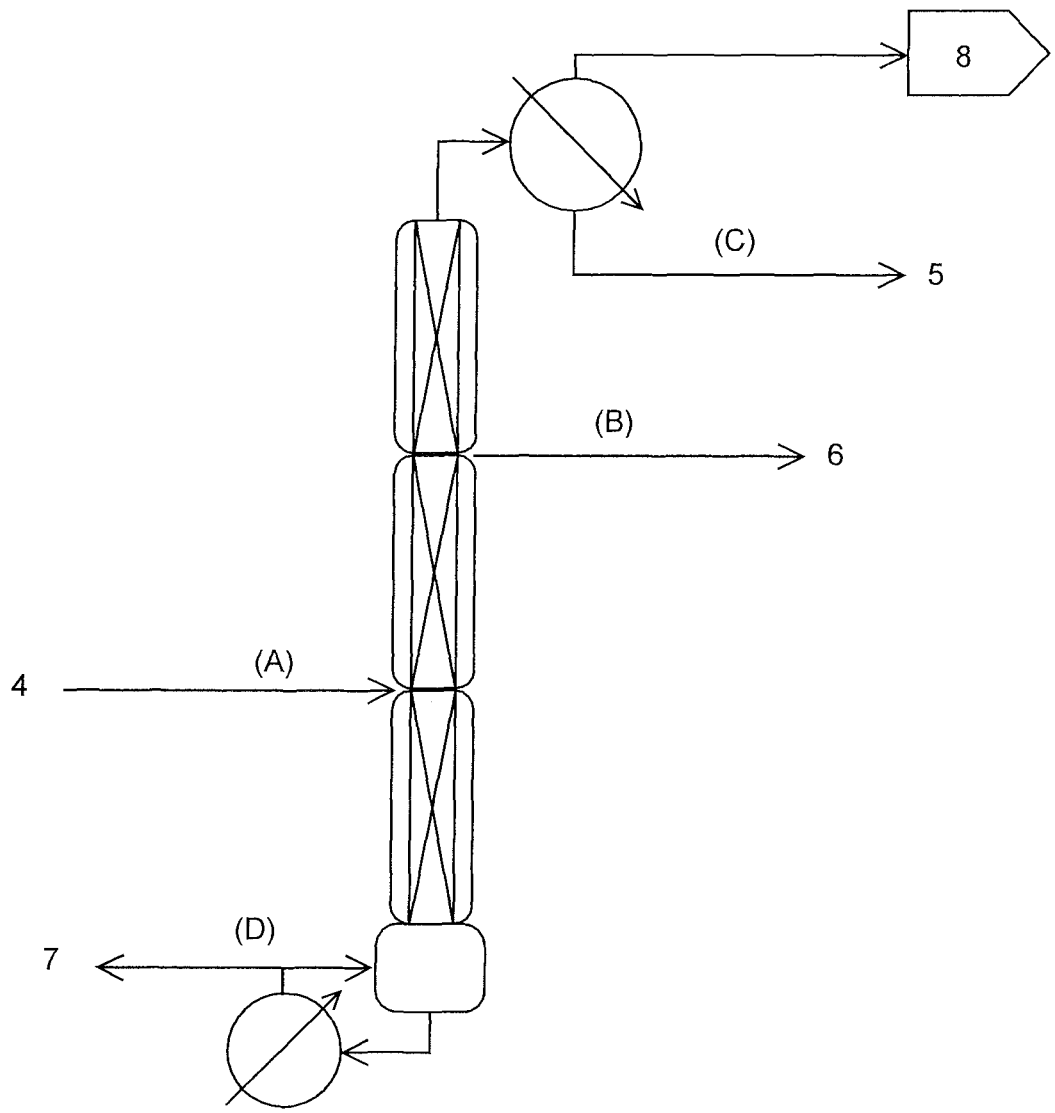
FIG. 2 schematically shows the second step (purification of lactic acid by distillation) of the process according to one embodiment of the present invention.

This step is characterized in that the concentrated lactic acid solution is subjected to distillation in a multistage column comprising three zones (FIG. 2) and contains packing that minimizes the hold up ("dead volume") and the pressure drops, this packing preferentially being of structured type. The heat input is provided by a reboiler positioned at the bottom of the column that makes it possible to minimize any thermal or chemical degradation, it will preferentially be a thin film evaporator with or without a scraped surface. The temperature of the wall of the evaporator is maintained between 80° C. and 200° C., preferentially between 100° C. and 180° C., more preferentially between 130° C. and 170° C. At the top of the column there is a condensation system and also a reflux system. The lactic acid from step 1 is fed into the column above the reboiler (A). The water and the volatile impurities are eliminated at the top of the column (C) whilst the purified lactic acid is extracted in liquid form via a side extraction located between the feed and the top of the column (B). Lastly, the heaviest molecules leave at the bottom of the column (D) and/or loop to the reboiler. The use of a single column makes it possible to greatly reduce the residence times and therefore the thermal and chemical degradation phenomena, thus improving the yield of the distillation and also the purity of the lactic acid (by preventing contamination).

The pressure is between $10^{-3}$ and 100 mbar absolute (mbara), preferentially between $10^{-1}$ and 20 mbar absolute (mbara), more preferentially between 1 and 10 mbar. The unit is duly operated in a temperature range of between 80° C. and 200° C. and a pressure of between $10^{-3}$ and 100 mbar absolute (mbara), preferentially in a temperature range of between 100° C. and 180° C. and a pressure of between $10^{-1}$ and 20 mbar absolute (mbara). More preferentially, the unit is operated in a temperature range of between 130° C. and 170° C. and a pressure of between 1 and 10 mbar absolute (mbara). According to an improved but nonessential variant of the present invention, the purification residue may be sent to a second distiller in which the temperature and pressure conditions are harsher. The lactic acid resulting from this post-distillation and that is partially purified may be recycled either to the feed of the main distiller, or upstream of the process.

The distiller residue may also advantageously be recycled, after hydrolysis to give lactic acid, directly into the inlet stream of the present invention or to one of the steps of the pre-purification in known processes for producing lactic acid (for example chromatography, ion-exchange resins, etc.). This recycling will be even easier since the volatile impurities responsible for the color have been eliminated during the distillation step.

Other details and distinctive features of the invention, given below as nonlimiting examples, emerge from the description as some possible embodiments thereof.

EXAMPLES

Example 1

The objective of this example is to prove the improvement in the quality of lactic acid by the process of the invention compared to the prior art.

A 15% lactic acid solution obtained from a fermentation medium, stripped of the biomass by filtration, of the color by passing over charcoal and also of the various ionic substances by passing over cationic and anionic resin, is separated into two streams: "control" and "invention".

In a first experiment, the "control" stream is concentrated in two steps to 100%, all the free water being eliminated, in accordance with patent EP 0 986 532. It is then fed to a scraped-surface thin film evaporator having an exchange area of 500 cm², surmounted by a condenser, in order to distill the lactic acid. The heat transfer fluid circulating in the evaporator is thermal oil at 150° C., the vacuum applied to the apparatus is 10 mbar absolute (mbara). The lactic acid to be distilled is supplied at a flow rate of one liter per hour using a peristaltic pump. The lactic acid is recovered with a yield of 56%.

In a second experiment, the "invention" stream is concentrated in a single step to 95% (i.e. 5% of residual water) in a falling film evaporator, it is then distilled on a column with structured packing of the Sulzer EX type. The distillation column is broken down into three zones: the zone going from the reboiler to the feed (FIG. 2, A) has a packing height that measures 5.5 cm, the zone from the feeder to the extraction (FIG. 2, B) has a packing height of 11 cm and the zone from the extraction to the top of the column also has a packing height of 11 cm. The 95% lactic acid is fed to the first third of the column, whilst the pure lactic acid is drawn off, in liquid form, at the second third using a peristaltic pump. The most volatile compounds are themselves recovered at the top of the column using a condenser equipped with a reflux system. The latter is configured in order to reflux the distillates in a proportion of 50%. At the bottom of the column, the reboiler consists of a scraped-surface thin film evaporator having an exchange area of 500 cm². The heat transfer fluid circulating in the evaporator is thermal oil at 170° C., the vacuum applied to the apparatus is 10 mbar absolute (mbara). The lactic acid to be distilled is supplied at a flow rate of one liter per hour using a peristaltic pump. The distillation yield is of the order of 53%.

The analytical results of the lactic acid distilled during these two first experiments are given in tables 1 and 2.

TABLE 1 main features of the "control" lactic acid and of the "invention" lactic acid after distillation

|   |   | [Lactic acid][a] (%) | Fresh Color (Hazen) | Heat Stability (Hazen) | [Water][b] (%) |
|---|---|---|---|---|---|
| Control | Distillate | 99.67 | 17 | 94 | 1.0 |
| Invention | Product of interest (FIG. 2, B) | 99.89 | 12 | 23 | 0.7 |

[a]Determined by titration
[b]Determined by Karl Fisher titration

TABLE 2 analysis of the organic impurities of the "control" lactic acid and
of the "invention" lactic acid after distillation

|  |  | [5-HMF] (c) (ppm) | [2-F] (c) (ppm) | [2FMK] (c) (ppm) | [MFA] (c) (ppm) | [Pyruvic acid](d) (g/l) | [Propionic acid](d) (g/l) |
|---|---|---|---|---|---|---|---|
| Control | Distillate | 41.28 | 15.69 | 0.27 | 1.09 | 0.46 | 2.58 |
| Invention | Product of interest (FIG. 2, B) | 0.73 | 2.17 | 6.06 | 1.03 | 0.17 | 2.41 |

(a) Determined by UV HPLC
(b) Determined by organic acid HPLC
5 HMF = 5-hydroxymethyl furfural
2-F = 2-furfural
2-FMK = 2-furyl methyl ketone
MFA = 5-methyl-2-furaldehyde For a same starting solution, it is observed that the purified lactic acid obtained by the process of the invention has a much better quality than the "control" result. Specifically, the color parameters ("Fresh Color" and "Heat Stability") are much lower for the "invention" lactic acid. A concentration nearly 6 times higher in molecules that absorb in the UV is observed for the "control" lactic acid (58.33 ppm in total versus 9.99 ppm for the lactic acid purified according to the invention). The impact on the concentration of pyruvic acid is also significant.

Example 2

In this second example, the same 15% lactic acid solution from example 1 is concentrated in a single step to 90% (i.e. 10% of residual water), it is then distilled on a column with structured packing of the Sulzer EX type according to the principle of the invention under the same conditions and on the same apparatus as those described in example 1. The distillation yield is of the order of 51%.

The analytical results of the distilled lactic acid are given in tables 3 and 4.

TABLE 3 main features of the lactic acid and of the
distillate obtained after treatment

|  |  | [Lactic acid](a) (%) | Fresh Color (Hazen) | Heat Stability (Hazen) | [Water](b) (%) |
|---|---|---|---|---|---|
| Invention | Product of interest (FIG. 2, B) | 99.73 | 11 | 18 | 0.8 |

(a) Determined by titration
(b) Determined by Karl Fisher titration

TABLE 4 analysis of the organic impurities of the lactic acid obtained after treatment

|  |  | [5-HMF] (c) (ppm) | [2-F] (c) (ppm) | [2FMK] (c) (ppm) | [MFA] (c) (ppm) | [Pyruvic acid](d) (g/l) | [Propionic acid](d) (g/l) |
|---|---|---|---|---|---|---|---|
| Invention | Product of interest (FIG. 2, B) | 0.69 | 2.34 | 7.09 | 0.89 | 0.18 | 2.02 |

(a) Determined by UV HPLC
(b) Determined by organic acid HPLC
5 HMF = 5-hydroxymethyl furfural
2-F = 2-furfural
2-FMK = 2-furyl methyl ketone
MFA = 5-methyl-2-furaldehyde It is observed that the lactic acid obtained by the process of the invention still has as good results as in example 1. Specifically, the color parameters ("Fresh Color" and "Heat Stability") are of the same order, and therefore much better than the product obtained by the "control" experiment, this being with a residual water concentration of 10%. The impact on the molecules that absorb in the UV is also confirmed.

Example 3

The purified "control" and "invention" lactic acids from example 1 are cyclized and purified according to the process described in patent EP 2 222 658.

The lactide obtained is then polymerized according to the process described in patent BE 1019059.

In this example, the "yellow index" makes it possible to characterize the purity of the PLA after polymerization. This is a number calculated from spectrophotometric data, which describes the changing color of a sample from colorless to yellow. According to the ASTM method, there is a definition of the whiteness and of the yellowness. The ASTM E-313-98 yellowness index is used to determine to what extent the color of a sample has shifted away from an ideal white. In the present case, the "yellow index" was measured on a BYK S 6836 spectro-guide sphere gloss. The analytical results of the "control" PLA and of the "invention" PLA are given in table 5.

TABLE 5 analysis of the color of the PLA

|  | Yellow Index |
| --- | --- |
| "Control" PLA | 8 |
| "Invention" PLA | 2 |

It is observed that the "invention" PLA has a lower yellow index than that of the "control" PLA, it is therefore less colored and is closer to a state of transparency.

REFERENCE MARKS 1 concentrating step
2 distillation step
3 aqueous lactic acid solution (LA concentration 5-15%)
4 concentrated lactic acid solution (LA concentration 85-95%)
5 water and volatile impurities
6 purified lactic acid
7 residue
8 vacuum

The invention claimed is:

1. A process for purifying an aqueous lactic acid solution, obtained from a fermentation medium or from any other source previously stripped of the solid substances and/or of the biomass optionally present and also of the ionic substances, wherein the process comprises:
   a. concentrating the lactic acid solution to a concentration between 85% and 95%, wherein 15% to 5% of free water is achieved; and
   b. separating, in a single step, the concentrated stream obtained in (a) into a stream comprising purified lactic acid, a stream comprising the volatile impurities and a stream comprising the heavier impurities.

2. The purification process as claimed in claim 1, wherein the concentrating step (a) is carried out on a thin film evaporator.

3. The purification process as claimed in claim 1, wherein the concentrating step (a) is carried out at reduced pressure, between 40 and 500 mbar.

4. The purification process as claimed in claim 1, wherein the separating step (b) is carried out in a distillation column.

5. The purification process as claimed in claim 1, wherein the stream comprising the purified lactic acid obtained in (b) is extracted in liquid form via a side extraction.

6. The purification process as claimed in claim 4, wherein the distillation column contains a structured or unstructured packing that minimizes the residence time and the pressure drops.

7. The purification process as claimed in claim 4, wherein the heat input of the distillation column is provided by a reboiler that makes it possible to minimize any thermal and chemical degradation.

8. The purification process as claimed in claim 7, wherein the reboiler will be a thin film evaporator with or without a scraped surface.

9. The purification process as claimed in claim 8, wherein the temperature in the reboiler is between 80° C. and 200° C.

10. The purification process as claimed in claim 4, wherein the distillation is carried out at a pressure of between $10^{-3}$ and 100 mbar absolute (mbara).

11. A process for purifying an aqueous lactic acid solution, obtained from a fermentation medium or from any other source previously stripped of the solid substances and/or of the biomass optionally present and also of the ionic substances, wherein the process consists in:
   a. concentrating the lactic acid solution to a concentration between 85% and 95%, wherein 15% to 5% of free water is achieved; and
   b. storing the concentrated solution obtained in (a) for a period not exceeding 24 h;
   c. separating, in a single step, the concentrated stream obtained in (a) and stored in (b) into a stream comprising purified lactic acid, a stream comprising the volatile impurities and a stream comprising the heavier impurities.

12. The purification process as claimed in claim 11, wherein the separating step (c) is carried out in a distillation column.

13. The purification process as claimed in claim 1, wherein the lactic acid solution derived from the concentrating step (a) is fed into a column, above a reboiler, the purified lactic acid is extracted, in liquid form, laterally between a feed and a top of the column, whilst eliminating the water and the volatile impurities at the top of the column and the heaviest molecules leave at a bottom of the column and/or loop to the reboiler.

14. The purification process as claimed in claim 1, wherein the distillation residue may be either hydrolysed or sent to a second distiller in order to be recycled either to the feed of the main distiller, or upstream of the process.

15. The purification process as claimed in claim 1, wherein in step (a) the lactic acid solution is concentrated to a concentration between 90% and 95%, wherein 10% to 5% of free water is achieved.

16. The purification process as claimed in claim 1, wherein the concentrating step (a) is carried out on a falling film evaporator.

17. The purification process as claimed in claim 1, wherein the separating step (b) is carried out in a rectifying column.

18. The purification process as claimed in claim 4, wherein the distillation is carried out at a pressure of between 1 and 10 mbar absolute (mbara).

19. The purification process as claimed in claim 11, wherein in step (a) the lactic acid solution is concentrated to a concentration between 90% and 95%, wherein 10% to 5% of free water is achieved.

20. The purification process as claimed in claim 11, wherein the separating step (c) is carried out in a rectifying column.

\* \* \* \* \*